United States Patent [19]

Beller et al.

[11] Patent Number: 5,663,410

[45] Date of Patent: Sep. 2, 1997

[54] CIS-4-(2,2,3,3-TETRAFLUOROPROPOXY)-CINNAMONITRILE AND TRANS-4-(2,2,3,3-TETRAFLUOROPROPOXY)-CINNAMONITRILE AND A PROCESS FOR THEIR PREPARATION

[75] Inventors: Matthias Beller, Idstein; Ralf Pfirmann, Griesheim, both of Germany

[73] Assignee: Hoechst Aktiengesellschaft, Frankfurt

[21] Appl. No.: 554,185

[22] Filed: Nov. 6, 1995

[30] Foreign Application Priority Data

Nov. 8, 1994 [DE] Germany .................. 44 39 836.0

[51] Int. Cl.$^6$ ................................... C07C 255/07
[52] U.S. Cl. ........................................... 558/401
[58] Field of Search ................................ 558/401

[56] References Cited

FOREIGN PATENT DOCUMENTS 0347066  3/1995  European Pat. Off. .

OTHER PUBLICATIONS

Boyle, F. T., et al, Am. NY Acad. Sci. 544:86–100 (1988) (Antifungal Drugs).

Primary Examiner—Johann Richter
Assistant Examiner—John Peabody, III
Attorney, Agent, or Firm—Connolly and Hutz

[57]  ABSTRACT

The present invention relates to the compounds cis-4-(2,2,3,3-tetrafluoropropoxy)cinnamonitrile and trans-4-(2,2,3,3-tetrafluoropropoxy)cinnamonitrile and to a process for their preparation. The process relates to the preparation of cis-4-(2,2,3,3-tetrafluoropropoxy)cinnamonitrile and trans-4-(2,2,3,3-tetrafluoropropoxy)cinnamonitrile or optionally one of these two compounds, by fractionally distilling a mixture containing cis- and trans-4-(2,2,3,3-tetrafluoropropoxy)cinnamonitrile under reduced pressure, separating off a main fraction containing at least 80% by weight of cis-4-(2,2,3,3-tetrafluoropropoxy)cinnamonitrile and a main fraction containing at least 80% by weight of trans-4-(2,2,3,3-tetrafluoropropoxy)cinnamonitrile, further purifying these main fractions by means of fractional crystallization or melt crystallization or adjusting one of these main fractions by isomerization to the cis/trans isomer ratio corresponding to the particular thermodynamic equilibrium and returning it to the process and returning the remaining fractions to the process directly or after isomerization.

5 Claims, No Drawings

CIS-4-(2,2,3,3-TETRAFLUOROPROPOXY)-CINNAMONITRILE AND TRANS-4-(2,2,3,3-TETRAFLUOROPROPOXY)-CINNAMONITRILE AND A PROCESS FOR THEIR PREPARATION

The present invention relates to the compounds cis-4-(2,2,3,3-tetrafluoropropoxy)cinnamonitrile and trans-4-(2,2,3,3-tetrafluoropropoxy)cinnamonitrile and to a process for their preparation.

According to Ann. N.Y. Acad. Sci (1988), 544, pages 86 to 100 (Chem. Abstr. 111, 208650), 4-tetrafluoropropoxycinnamonitrile can be prepared in the following manner. 4-Fluorobenzonitrile is reacted with 2,2,3,3-tetrafluoropropanol to give 4-(2,2,3,3-tetrafluoropropoxy)benzonitrile which is then reduced by complex hydrides to give 4-(2,2,3,3-tetrafluoropropoxy) benzaldehyde. The 4-(2,2,3,3-tetrafluoropropoxy) benzaldehyde leads to the 4-tetrafluoropropoxycinnamonitrile by reaction with the anion of diethyl cyanomethylphosphonate in the context of a Wittig-Horner reaction.

However, the 4-tetrafluoropropoxycinnamonitrile always arises in this reaction as a mixture of the geometric isomers, that is as a cis/trans isomer mixture. This cis/trans isomer mixture can be used as starting material for the industrial preparation of antimycotics. However, all of the disadvantages which are inevitably associated with the use of a cis/trans isomer mixture have to be accepted in this case. Disadvantages which may be mentioned in comparison with an isomerically pure compound are, for example, the variable contents, due to preparation and workup, of the particular geometric isomers and the differing activity of the geometric isomers in the particular pharmaceutically active end product.

Isomerically pure derivatives of 4-(2,2,3,3-tetrafluoropropoxy)cinnamic acid, in particular (E)-4-(2,2,3,3-tetrafluoropropoxy)cinnamide and a triazole derivative which can be prepared therefrom, are used in the preparation of fungicides (EP 0 472 392). However, the synthetic pathway followed in this case is associated with very high expense.

In a first step, p-chlorobenzonitrile is reacted with 2,2,3,3-tetrafluoropropanol in the presence of bases, for example sodium hydride, with exchange of the p-chlorine atom to give 4-(2,2,3,3-tetrafluoropropoxy)benzonitrile. The second step is to reduce the 4-(2,2,3,3-tetrafluoropropoxy) benzonitrile by metal hydrides, for example diisobutylaluminum hydride, 4-(2,2,3,3-tetrafluoropropoxy) benzaldehyde being formed. The 4-(2,2,3,3-tetrafluoropropoxy)benzaldehyde is reacted stereoselectively with ethyl diethylphosphonoacetate in a third reaction step to give ethyl (E)-4-(2,2,3,3-tetrafluoropropoxy)cinnamate.

In a subsequent further reaction stage, ethyl (E)-4-(2,2,3,3-tetrafluoropropoxy)cinnamate is saponified with aqueous sodium hydroxide solution and (E)-4-(2,1,3,3-tetrafluoropropoxy)cinnamic acid is obtained by acidification and extraction.

From (E) -4-(2,2,3,3 -tetrafluoropropoxy) cinnamic acid, by reaction with thionyl chloride, the corresponding (E)-4-(2,2,3,3-tetrafluoropropoxy)cinnamoyl chloride (fifth step) is obtained which in a concluding sixth step, by reaction with ammonia, gives (E)-4-(2,2,3,3-tetrafluoropropoxy) cinnamide. From (E)-4-(2,2,3,3-tetrafluoropropoxy) cinnamide, with ring closure at the amide group, a triazole derivative is then formed, that is 3-[(E)-4-(2,2,3,3-tetrafluoropropoxy)styryl]- 1H-1,2,4 -triazole. The triazole serves as an important building block for the preparation of fungicides. The synthetic pathway outlined above is described in more detail in EP 0 472 392 on page 10, line 42 to page 11, line 6 and in Examples 1 to 6 on pages 14 to 16.

The observations above verify that in general there is a lively interest in preparing 4-(2,2,3,3-tetrafluoropropoxy) cinnamic acid derivatives in isomerically pure form and further processing them. In this case also, as described in EP 0 472 392, a highly complicated synthetic pathway which is demanding in terms of equipment is accepted.

In this context, it is a worthwhile object to provide further 4-(2,2,3,3-tetrafluoropropoxy)cinnamic acid derivatives in isomerically pure or substantially isomerically pure form.

This object is achieved by the compounds cis-4-(2,2,3,3-tetrafluoropropoxy)cinnamonitrile and trans-4-(2,2,3,3-tetrafluoropropoxy)cinnamonitrile.

In order that this may be more readily understood, both compounds are reproduced below together with their formulae:

cis-4-(2,2,3,3-tetrafluoropropoxy)cinnamonitrile (A)

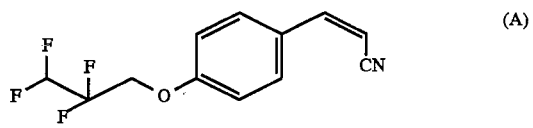

and trans-4-(2,2,3,3-tetrafluoropropoxy)cinnamonitrile (B)

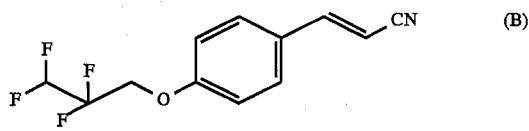

From these cis-and trans-nitriles, the corresponding cis- and trans-4-(2,2,3,3 -tetrafluoropropoxy)cinnamides may be prepared, for example by addition of water.

A further object of interest is to make available in isomerically pure form or substantially isomerically pure form the compounds cis-4-(2,2,3,3-tetrafluoropropoxy) cinnamonitrile and trans-4-(2,2,3,3-tetrafluoropropoxy) cinnamonitrile in a simple manner and starting from a comparatively readily accessible starting material.

This object is achieved by a process for the preparation of cis-4-(2,2,3,3-tetrafluoropropoxy)cinnamonitrile and trans-4-(2,2,3,3-tetrafluoropropoxy)cinnamonitrile or optionally of one of these two compounds. It comprises fractionally distilling a mixture containing cis- and trans-4-(2,2,3,3-tetrafluoropropoxy)cinnamonitrile under reduced pressure, separating off a main fraction containing at least 80% by weight of cis-4-(2,2,3,3-tetrafluoropropoxy)cinnamonitrile and a main fraction containing at least 80% by weight of trans-4-(2,2,3,3-tetrafluoropropoxy)cinnamonitrile, further purifying these main fractions by means of fractional crystallization or melt crystallization or adjusting one of these main fractions by isomerization to the cis/trans isomer ratio corresponding to the particular thermodynamic equilibrium and returning it to the process and returning the remaining fractions to the process directly or after isomerization.

An important advantage of the process according to the invention is that one does not have to rely on a highly complex, stereoselective synthesis in which it is established from the beginning whether cis- or trans-4-(2,2,3,3-tetrafluoropropoxy)cinnamonitrile is prepared. Rather, any mixture containing cis-and trans-4-(2,2,3,3-tetrafluoropropoxy)cinnamonitrile can be used as starting material.

Such mixtures are accessible in good yield by a comparatively very simple process which is the subject matter of an application (DE 44 08 083) which has an earlier priority but had not been published at the time of the present application.

For the sake of completeness, this process may be considered in rather more detail at this point.

DE 44 08 083 relates to a process for the preparation of 4-fluoroalkoxycinnamonitriles of the formula (I)

in which n=1 to 8 and m=1 to 17, where m≦2n+1, by reacting 4-fluorobenzaldehyde with a fluoroalkanol of the formula (II),

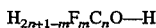

in which m and n have the meanings given above, in the presence of a base and if appropriate a solvent, and reacting the resulting 4-fluoroalkoxybenzaldehyde with cyanoacetic acid or an alkyl cyanoacetate in the presence of a base and optionally a solvent.

The process may be carried out as follows:

4-Fluorobenzaldehyde is reacted with the fluoroalkanol in the presence of 0.5 to 3, in particular 0.6 to 1.25 equivalents of base at temperatures between 10° C. and 180° C., in particular 60° to 155° C., to give the corresponding 4-fluoroalkoxybenzaldehyde. Bases which are suitable are, e.g., alkali metal carbonates, in particular potassium carbonate, sodium carbonate or mixtures of potassium carbonate and sodium carbonate. The reaction can be carried out both in the presence of dipolar aprotic solvents such as N,N-dimethylacetamide, sulfolane and N,N-dimethylformamide and in the absence of solvent. In the latter case, the procedure is advantageously performed in an excess of fluoroalkanol which ultimately acts as solvent. The dosage of fluoroalkanol must be chosen as a factor of the amount of base used in such a way that the reaction mixture remains stirrable and is advantageously 0.8 to 1.5 equivalents based on the 4-fluorobenzaldehyde used.

Two routes are suitable for the workup of the resulting reaction mixture:

1) The reaction mixture is separated off from the salts present (excess base and base fluoride formed) by filtration. The product is then distilled from the filtrate.
2) Alternatively thereto, it is possible to dissolve the base fluoride formed and salt present in excess by addition of water, to separate the phases formed and either to directly introduce the product situated in the organic phase into the following reaction or if necessary to purify it by distillation. Products situated in the aqueous phase can be extracted by solvents such as toluene, chlorobenzene, dichlorobenzene, methylene chloride or tert-butyl methyl ether.

The 4-fluoroalkoxybenzaldehyde obtained is then reacted with 0.3 to 4 equivalents, preferentially with 0.6 to 2.0 equivalents, preferably with 0.8 to 1.2 equivalents, of cyanoacetic acid or alkyl cyanoacetates at temperatures of 50° to 250° C., preferably 80° to 180° C., in the presence of a base or a basic catalyst to give 4-fluoroalkoxycinnamonitrile.

Alkyl cyanoacetates which have proved to he useful are methyl cyanoacetate, ethyl cyanoacetate and propyl cyanoacetate. The base or basic catalyst which can be used is aromatic and aliphatic amines, alkali metal carbonates and alkaline earth metal carbonates or basic oxides and hydroxides such as NaOH, KOH or $Al_2O_3$.

Compounds which have proved useful in many cases as base and if appropriate also as solvent are amines such as pyridine, piperidine, morpholine, tributylamine, triethylamine, tripropylamine, benzylamine, aniline and dialkylaniline.

The reaction with cyanoacetic acid derivatives can be carried out in the absence of solvents, but it can also be advantageous to perform the reaction in the presence of solvents. Compounds which can serve as solvents can be, for example, aromatics such as benzene, toluene, xylenes, dipolar aprotic solvents such as dimethylformamide, dimethylacetamide, dimethyl sulfoxide, sulfolane, alcohols such as ethanol, propanol, butanol and glymes or ethers such as diglyme. The amount of solvent is 5 to 90% by weight, based on the amount of 4-fluoroalkoxybenzaldehyde used. To prepare 4-(2,2,3,3-tetrafluoropropoxy)cinnamonitrile, 4-fluorobenzaldehyde is reacted with 2,2,3,3-tetrafluoropropanol as fluoroalkanol in the process described above and the procedure is otherwise carried out as described above.

In this manner, a mixture containing cis-4-(2,2,3,3-tetrafluoropropoxy)cinnamonitrile and trans-4-(2,2,3,3-tetrafluoropropoxy)cinnamonitrile is obtained which can be used as starting material in the process according to the invention. In addition to using a cis/trans isomer mixture, the process according to the invention additionally has a further considerable advantage. That is, it permits, depending on desire and requirement, not only the preparation of cis-4-(2,2,3,3-tetrafluoropropoxy)cinnamonitrile or trans-4-(2,2,3,3-tetrafluoropropoxy)cinnamonitrile, but also exclusively or predominantly one of the two isomers at the expense of the respective isomer not required. If, for example, the cis isomer is required, the process according to the invention enables a conversion of trans-4-(2,2,3,3-tetrafluoropropoxy) cinnamonitrile into the corresponding cis isomer and its subsequent separation as a pure product. On the other hand, if the trans isomer is wanted, the process according to the invention enables conversion of cis-4-(2,2,3,3-tetrafluoropropoxy)cinnamonitrile into the trans isomer and its subsequent separation as a pure product.

By this means, a highly flexible adaptation to the particular requirement of one or the other isomer is possible without the respective isomer not required arising as an unwanted byproduct.

The process according to the invention can be applied to mixtures which contain cis-and trans-4-(2,2,3,3-tetrafluoropropoxy)cinnamonitrile in any ratio. Depending on composition of the mixture used as starting material, the cis- and trans-4-(2,2,3,3-tetrafluoropropoxy)cinnamonitrile is obtained in a purity of at least 95, in particular 97.5, %. However, purities of 99% and above can also be achieved.

Usually, a mixture is used which contains cis- and trans-4-(2,2,3,3-tetrafluoropropoxy)cinnamonitrile in a molar ratio of 75:25 to 25:75, in particular 70:30 to 50:50, preferably 65:35 to 60:40.

The cis/trans isomer mixture is fractionally distilled under comparatively mild conditions. The distillation column used for the fractionation must have sufficient separation power, for example 15 to 20 theoretical plates.

It is surprising that despite the comparatively high temperatures, which are unavoidable in this distillation because of the high polarity and high molecular mass of the cis- and trans-4-(2,2,3,3-tetrafluoropropoxy)cinnamonitrile, no decomposition occurs or at any rate very slight decomposition occurs. In addition, it could not be anticipated that the desired cis or trans isomer would be successfully accumulated to such an extent that a high to very high purity may be achieved by means of a further purification stage. A purity of at least 95% may be achieved without problem. A purity of at least 97.5% is also not unusual. Even purities such as are required for the further processing of the isomers to give pharmaceutically active substances, that is 99% or more, may be achieved.

In the distillation, excessively high temperatures must be avoided, as must be excessively long residence times, since excessive temperatures, as do excessive residence times, lead to the formation of unwanted byproducts which can be removed from the desired product of value only with great difficulty or not at all.

The distillation is performed at reduced pressure, usually at 0.01 to 50, in particular 1 to 30, preferably 5 to 10, mbar. In order to avoid an excessive loading, it is advisable not to select an excessively high reflux ratio in the distillation. Generally, a reflux ratio of 2:1 to 1:4, in particular 1:1 to 1:2, proves to be sufficient. The distillation conditions are chosen in such a way that a main fraction containing at least 80% by weight of cis-4-(2,2,3,3-tetrafluoropropoxy) cinnamonitrile and /or a main fraction containing at least 80% by weight of trans-4-(2,2,3,3-tetrafluoropropoxy) cinnamonitrile can be separated off. In the course of the distillation, cis-4-(2,2,3,3-tetrafluoropropoxy) cinnamonitrile passes overhead as the first product, trans-4-(2,2,3,3-tetrafluoropropoxy)cinnamonitrile accumulates in the bottom product. trans-4-(2,2,3,3-Tetrafluoropropoxy) cinnamonitrile can be distilled off from the bottom product and the distillate or else a suitably enriched bottom product can be further processed as the main fraction.

Usually, a main fraction containing 80 to 95% by weight, in particular 85 to 90% by weight, of cis-4-(2,2,3,3-tetrafluoropropoxy)cinnamonitrile and a main fraction containing 80 to 95% by weight, in particular 85 to 90% by weight, of trans-4-(2,2,3,3-tetrafluoropropoxy) cinnamonitrile are separated off. In addition to the main fractions, other fractions arise. These remaining fractions are the first runnings fractions, intermediate runnings fractions and distillation residues.

For further purification, the main fraction is subjected either to a fractional crystallization or to a melt crystallization. The technique of melt crystallization is described in more detail, for example, in Ullmann's Encyclopedia of Industrial Chemistry, Vol. B2, pages 3–29 to 3–34, 5th Edition (1988).

For fractional crystallization, the product to be purified (main fraction) is dissolved as appropriate at elevated temperature in an organic solvent and the crystallization is induced by concentration and /or cooling.

The temperature at which the product to be purified is dissolved also depends on the particular solvent used and the particular concentration of the resulting solution.

Generally, the product (main fraction) to be purified is dissolved at 20° to 180° C., in particular 60° to 150° C. Suitable solvents are halogenated or nonhalogenated aromatic or aliphatic hydrocarbons, alcohols, alkyl ethers or alkyl esters. A mixture of these solvents may also be used.

Without making any claim as to completeness, suitable solvents which may be mentioned are toluene, o-xylene, m-xylene, p-xylene, mixtures of isomeric xylenes, chlorobenzene, chlorotoluene, hexane, heptane, octane, mixtures of various aliphatic hydrocarbons having 5 to 10 carbon atoms, dichloromethane, trichloromethane, 1,2-dichloroethane, methanol, ethanol, n-propanol, i-propanol, n-butanol, i-butanol, mixtures of aliphatic alcohols having 1 to 3 carbon atoms with water, methyl tert-butyl ether, diethyl ether, di-n-propyl ether, di-n-butyl ether, ethyl acetate, propyl acetate, butyl acetate or mixtures of the abovementioned solvents. Solvents which are particularly suitable are toluene, o-xylene, m-xylene, p-xylene, mixtures of isomeric xylenes, chlorobenzene, chlorotoluene, dichloromethane, trichloromethane, 1,2-dichloroethane, methanol, ethanol, n- and i-propanol, n-and i-butanol and mixtures of the abovementioned solvents.

Another possible method of further purifying the main fraction is offered by melt crystallization, the different variants of which, as already mentioned, are described, for example, in Ullmann's Encyclopedia of Industrial Chemistry, Vol. B2, pages 3–29 to 3–34, 5th Edition (1988).

In order to carry out the melt crystallization, the main fractions are crystallized, they are exposed in the crystalline state to a gradual temperature increase and the molten constituents resulting in the course of this are separated off.

According to a special variant, the product to be purified (main fraction) is charged into a vertically upright, thermostatable tube, for example an empty distillation column, and the product is brought to crystallization, for example by cooling and optionally with addition of seed crystals.

The vertically upright tube is then gradually heated by means of the thermostating device and the temperature is gently increased. As a result of the action of heat, molten constituents are formed which exit from the crystalline main fraction and drip off. One isomer is preferably contained in the exiting drops, while the other isomer preferably accumulates in the remaining residue. In this manner, the main fractions arising from the distillation which contain either cis-4-(2,2,3,3-tetrafluoropropoxy)cinnamonitrile or trans-4-(2,2,3,3-tetrafluoropropoxy)cinnamonitrile in enriched form, may be further purified in a gentle manner.

It is particularly surprising that in the purification of a main fraction containing trans-4-(2,2,3,3-tetrafluoropropoxy)cinnamonitrile by melt purification, it is not the cis-4-(2,2,3,3-tetrafluoropropoxy)cinnamonitrile melting at higher temperature which remains as crystals in the residue, but the trans-4-(2,2,3,3-tetrafluoropropoxy) cinnamonitrile melting at lower temperatures, while the cis-4-(2,2,3,3-tetrafluoropropoxy)cinnamonitrile which melts at higher temperature drips off molten in enriched form.

Therefore, melt crystallization is particularly suitable for the preparation of pure trans-4-(2,2,3,3-tetrafluoropropoxy) cinnamonitrile.

The process according to the invention, as already described above, permits preparation as desired of cis-4-(2, 2,3,3-tetrafluoropropoxy)cinnamonitrile or trans-4-(2,2,3,3-tetrafluoropropoxy)cinnamonitrile by the conversion (isomerization) of the respective isomer or isomer mixture not required into the desired isomer or isomer mixture. If necessary, one of the two main fractions, that is the fraction which contains the isomer which is not desired, and /or the remaining fractions which contain the cis and trans isomers in differing ratios according to their origin as first runnings fractions, intermediate runnings fractions or distillation residue is subjected to a photochemical isomerization using light and /or to a thermal isomerization using heat in the presence of a base.

In the photochemical isomerization the material to be isomerized is irradiated using a suitable light source, for example a conventional UV radiator or illumination apparatus known from the literature which is equipped, for example, with high-pressure mercury lamps or medium-pressure mercury lamps. See J. Kagan, Organic Photochemistry, Principles and Applications (Academic Press, London (1993)) for the irradiation technique.

It is usually sufficient to carry out the isomerization with light of a wavelength of 100 to 500, in particular 150 to 360, preferably 180 to 320, mm. If the intention is to carry out isomerization thermally, the isomerization is usually carried out at 30 to 170, in particular 60° to 140, °C. in the presence of a nitrogen-containing base or a mixture of nitrogen-containing bases. The base used is a nitrogen-containing, heterocyclic compound, an aliphatic, cycloaliphatic, araliphatic or aromatic amine or a mixture of these substances. Without making any claim as to completeness, suitable bases which may be mentioned are pyrrolidone, piperidine, piperazine, pyridine, morpholine, triethylamine, tripropylamine, tributylamine, a dialkylaniline, aniline, benzylamine or a mixture of these substances.

The isomerization can be carried out solely using light or solely using heat and in the presence of a base. However, it is also possible to employ these two types of isomerization in any sequence one after the other or alternatively simultaneously.

Depending on the type and length of the isomerization, an isomer ratio is established corresponding to the particular thermodynamic equilibrium. The isomerized product is then reused in the process and fed to the fractional distillation.

When the process according to the invention is carried out, fractions also arise which do not need to be isomerized. These product mixtures can be reused directly in the process and can be passed directly to the fractional distillation.

The process according to the invention can be carried out continuously or discontinuously. A discontinuous process procedure proves to be particularly simple.

The examples below describe the invention without restricting it.

Experimental section:

Preparation of 4-(2,2,3,3-tetrafluoropropoxy) cinnamonitrile (cis/trans isomer mixture)

A mixture of 500 g of 4-(2,2,3,3-tetrafluoropropoxy) benzaldehyde, 183 g of cyanoacetic acid, 250 ml of pyridine and 250 ml of piperidine are heated with stirring and allowed to react for 1 hour at 110° C. A further 36.6 g of cyanoacetic acid are then added and the mixture is allowed to react for a further 30 minutes at 110° C. The reaction mixture is cooled, distilled under reduced pressure and 433.1 g of 4-(2,2,3,3-tetrafluoropropoxy)cinnamonitrile are obtained (yield: 78%; purity 95%) in the form of a mixture of isomers which contains cis-4-(2,2,3,3-tetrafluoropropoxy) cinnamonitrile and trans-4-(2,2,3,3-tetrafluoropropoxy) cinnamonitrile in a molar ratio cis:trans of approximately 1.35 to 1.8:1 (corresponding to a weight ratio of about (58 to 64):(42 to 36)) and in addition up to about 3% by weight of piperidine and 2% by weight of unidentified impurities and resins.

EXAMPLE 1

Fractional distillation of 4-(2,2,3,3-tetrafluoropropoxy) cinnamonitrile (cis/trans isomer mixture)

The fractional distillation is carried out using a silvered fractionating column of 100 cm in length (diameter 5 cm) which is filled with packings (Sulzer CX type). The separation efficiency of this column corresponds to 15 to 18 plates, determined by trial distillation of a test mixture.

897 g of a cis/trans isomer mixture prepared in accordance with Example 1 which contains cis-4-(2,2,3,3-tetrafluoropropoxy)cinnamonitrile and trans-4-(2,2,3,3-tetrafluoropropoxy)cinnamonitrile in a molar ratio cis:trans of about (1.35 to 1.8):1 (corresponding to a weight ratio of about (58 to 64):(42 to 36)), and in addition up to about 3% by weight of piperidine and 2% by weight of unidentified impurities and resins, are used. The product stream taken off and the respective reflux arising are controlled via a liquid divider unit.

The pressures and temperatures quoted always relate to the top of the fractionating column.

1st fraction: To 5 mmHg (6.7 mbar) and 136° to 138° C., 23.9 g arise which contain 62.2% by weight of cis-4-(2,2, 3,3-tetrafluoropropoxy)cinnamonitrile. The reflux ratio is 3:2.

2nd fraction: From 5 mmHg (6.7 mbar) and 138° C. to 5 mmHg (6.7 mbar) and 158° C., 356.0 g arise of a main fraction which contains 81.3% by weight of cis-4-(2,2,3,3-tetrafluoropropoxy)cinnamonitrile and 18.7% by weight of trans-4-(2,2,3,3-tetrafluoropropoxy)cinnamonitrile. The reflux ratio is 3:2.

3rd fraction: At 4 mmHg (5.3 mbar) and 158° to 161° C., 111.0 g arise of intermediate runnings which contain 50% by weight each of cis- and trans-4-(2,2,3,3-tetrafluoropropoxy) cinnamonitrile. The reflux ratio is 1:3.

4th fraction: At 4 mmHg (5.3 mbar) and 161° C., 49.2 g of intermediate runnings arise which contain 76.2% by weight of trans-4-(2,2,3,3-tetrafluoropropoxy) cinnamonitrile and 23.8% by weight of cis-4-(2,2,3,3-tetrafluoropropoxy)cinnamonitrile. The reflux ratio is 1:1.

5th fraction: From 3 mmHg (4 mbar) and 159° C. to 3 mmHg (4 mbar) and 164° C., 209.6 g arise of a main fraction which contains 80.5% by weight of trans-4-(2,2,3,3-tetrafluoropropoxy)cinnamonitrile and 19.5% by weight of cis-4-2,2,3,3-tetrafluoropropoxy)cinnamonitrile. The reflux ratio is 1:1.

6th residue: After separating off the main fraction, the distillation is terminated, in order not to increase further the thermal loading of the bottom product. 117 g of bottom product remain which contains about 80% by weight of 4-(2,2,3,3-tetrafluoropropoxy)cinnamonitrile (ratio of cis/trans isomers about 1:4) and about 20% by weight of unidentified substances. In the column packings, there are about a further 30 g of product.

Both the bottom product and the product still present in the column packings can be used in a further fractional distillation.

The degree of decomposition is about 3% of the starting product (determined by calibrated gas-chromatographic analysis) and is thus very low. In the bottom, there is still no carbonization on the wall, as can be observed in the case of fractional distillation of comparable products, which may be taken as an indicator of a sufficiently gentle fractional distillation procedure.

EXAMPLE 3a

Fractional crystallization of a main fraction containing trans-4-(2,2,3,3-tetrafluoropropoxy)cinnamonitrile 100 g of the main fraction arising from Example 2 as 5th fraction are dissolved at 100° to 140° C. in 300 g of xylene. The mixture is then allowed to cool slowly to 20° C. and the crystals are separated from the mother liquor. This operation is repeated two to three times, at first 280, then 230 and finally 200 g of xylene being used. In this manner, trans-4-(2,2,3,3-tetrafluoropropoxy)cinnamonitrile may be obtained in a purity of 98% and in 75% yield (=̂61.5 g).

EXAMPLE 3b

Fractional crystallization of a main fraction containing cis-4-(2,2,3,3-tetrafluoropropoxy)cinnamonitrile The procedure as given in Example 3 is followed, but 100 g are used of a main fraction, prepared similarly to Example 2, which contains 80% by weight of cis-4-(2,2,3,3-tetrafluoropropoxy)cinnamonitrile. By multiple repetition of the crystallization, cis-4-(2,2,3,3-tetrafluoropropoxy)cinnamonitrile is obtained in a purity of 98.4% and a yield of 76.3% (60.1 g).

EXAMPLE 4a

Melt crystallization of a main fraction containing trans-4-(2,2,3,3-tetrafluoropropoxy)cinnamonitrile 200 g are used of a main fraction prepared similarly to Example 2, which contains 80% by weight of trans-4-(2,2,3,3-tetrafluoropropoxy)cinnamonitrile, in a vertically upright thermostatable column (diameter: 4 cm) and the fraction is crystallized with cooling to 5° C. In order to reinforce the crystallization in the column, seed crystals can be added. Apart from an outlet valve at the bottom, the column contains no internals.

After crystallization has proceeded, heating of the column starts using the thermostating device. The melt crystallization begins at a temperature of 42° to 45° C. and is performed up to a temperature of 50° to 52° C.

The yield of pure trans-4-(2,2,3,3-tetrafluoropropoxy)cinnamonitrile which can be achieved by melt crystallization of a trans-4-(2,2,3,3-tetrafluoropropoxy)cinnamonitrile main fraction is usually lower than the yield of cis compound which can be achieved by melt crystallization of a cis-4-(2,2,3,3-tetrafluoropropoxy)cinnamonitrile main fraction, since the trans compound (solidification point: 50.6° C., measured on <99% pure trans-4-(2,2,3,3-tetrafluoropropoxy)cinnamonitrile) has a lower melting point or solidification point than the cis compound (solidification point: 53.95° C., measured on <99% pure cis-4-(2,2,3,3-tetrafluoropropoxy) cinnamonitrile).

However, surprisingly, when a trans-4-(2,2,3,3-tetrafluoropropoxy)cinnamonitrile main fraction is used, from a temperature of about 42° to 44° C., the cis-4-(2,2,3,3-tetrafluoropropoxy)cinnamonitrile which melts at a higher temperature begins to drip off first, the trans isomer accumulating in the residue.

About 50% of the starting material is obtained in the form of various fractions which contain between about 40 to 90% by weight of trans-4-(2,2,3,3-tetrafluoropropoxy)cinnamonitrile and correspondingly 60 to 10% by weight of cis-4-(2,2,3,3-tetrafluoropropoxy)cinnamonitrile.

The remaining material contains less than 5% by weight of the cis isomer and more than 95% by weight of trans-4-(2,2,3,3-tetrafluoropropoxy)cinnamonitrile.

EXAMPLE 4b

Melt crystallization of a main fraction containing cis-4-(2,2,3,3-tetrafluoropropoxy)cinnamonitrile 200 g are used of a main fraction prepared similarly to Example 2 which contain 80% by weight of cis-4-(2,2,3,3-tetrafluoropropoxy)cinnamonitrile, in a vertically upright thermostatable column (diameter: 4 cm) and the fraction is crystallized with cooling to 5° C. In order to reinforce the crystallization in the column, seed crystals can be added. Apart from an outlet valve at the bottom, the column contains no internals.

After crystallization has proceeded, heating of the column using the thermostating device. The melt crystallization begins at a temperature of 42° to 45° C. and is performed up to a temperature of 52° to 54° C.

The yield of pure cis-4-(2,2,3,3-tetrafluoropropoxy)cinnamonitrile is usually higher than the yield of trans compound, since the cis compound (solidification point: 53.95° C., measured on <99% pure cis-4-(2,2,3,3-tetrafluoropropoxy)cinnamonitrile) has a higher melting point or solidification point than the trans compound (solidification point: 50.6° C., measured on <99% pure trans-4-(2,2,3,3-tetrafluoropropoxy)cinnamonitrile).

As expected, as the temperature increases, from about 42° to 44° C., the trans-4-(2,2,3,3-tetrafluoropropoxy)cinnamonitrile which melts at low temperature begins to drip off first, the cis isomer accumulating in the residue.

About 40% of the starting material is obtained in the form of various fractions which contain between about 40 to 90% by weight of cis-4-(2,2,3,3-tetrafluoropropoxy)cinnamonitrile and correspondingly 60 to 10% by weight of trans-4-(2,2,3,3-tetrafluoropropoxy)cinnamonitrile.

The remaining material (118 g) contains less than 5% by weight of trans-4-(2,2,3,3-tetrafluoropropoxy)cinnamonitrile and more than 95% by weight of cis-4-(2,2,3,3-tetrafluoropropoxy)cinnamonitrile.

If the melt crystallization is continued and a lower yield (60 g $\hat{=}$ 30%) is accepted, the purity of the cis-4-(2,2,3,3-tetrafluoropropoxy)cinnamonitrile can be increased to 99% or above.

The cis/trans isomers are characterized in more detail below on the basis of spectroscopic data, all figures relating in each case to a product having >99% purity.

cis-4-(2,2,3,3-Tetrafluoropropoxy)cinnamonitrile (purity >99% by weight): solidification point: 53.95° C.

$^1$H-NMR (CDCl$_3$, TMS): 4.40 (ttr, J=11.5, 1.5 Hz, OC$\underline{H}_2$—CF$_2$) 5.37 (d, J=12.1 Hz,=C$\underline{H}$—CN) 6.06 (dt, J=52.4, 4.8 Hz, —CF$_2\underline{H}$) 6.98 (m, J=8.8 Hz, Ar—$\underline{H}^{3.5}$) 7.06 (d, J=12.1 Hz, Ar—C$\underline{H}$==) 7.82 (m, J=8.8 Hz, Ar—$\underline{H}^{2.6}$)

$^{19}$F-NMR (CDCl$_3$, CFCl$_3$):–125.3 (m, J=11.5, 4.8 Hz, —C$\underline{F}_2$—) –139.6 (dtr, J=52.4, 1.5 Hz, —C$\underline{F}_2$H)

GC-MS (purity>99.5%), m/z (%): 45 (2.7), 46 (2.3), 50 (14.0), 51 (85.6), 52 (5.8), 53 (2.5), 61 (4.9), 62 (15.4), 63 (42.7), 64 (23.3), 65 (9.6), 66 (2.9), 69 (3.4), 74 (9.4), 75 (20.7), 76 (11.1), 77 (21.6), 78 (3.0), 82 (2.8), 86 (1.1), 87 (4.4), 88 (12.7), 89 (100), 90 (22.7), 91 (2.4), 92 (1.8), 95 (3.8), 99 (2.1), 100 (2.4), 101 (46.2), 102 (14.2), 103 (23.6), 104 (3.0), 114 (6.1), 115 (9.4), 116 (81.3), 117 (13.1), 118 (2.7), 126 (1.4), 127 (8.7), 128 (60.8), 129 (6.8), 130 (26.8), 131 (7.1), 140 (1.1), 144 (29.5), 145 (6.4), 158 (56.8), 159 (6.7), 160 (2.3), 200 (5.2), 259 (96.9, M*), 260 (13.6)

trans-4-(2,2,3,3-Tetrafluoropropoxy)cinnamonitrile (purity>99% by weight):
solidification point: 50.6° C.

$^1$H-NMR (CDCl$_3$, TMS): 4.39 (ttr, J=11.5, 1.3 Hz, OC$\underline{H}_2$—CF$_2$) 5.77 (d, J=16.7 Hz, =C$\underline{H}$—CN) 6.05 (dt, J=52.6, 4.6 Hz,—CF$_2\underline{H}$) 6.96 (m, J=8.7 Hz, Ar—$\underline{H}^{3.5}$) 7.34 (d, J=16.7 Hz, Ar—C$\underline{H}$==) 7.44 (m, J=8.7 Hz, Ar—$\underline{H}^{2.6}$)

$^{19}$F-NMR (CDCl$_3$, CFCl$_3$):–125.1 (m, J=11.5, 4.6,—C$\underline{F}_2$—) –139.4 (dtr, J=52.6, 1.3, C$\underline{F}_2$H)

GC-MS (purity>99.5%), m/z (%): 45 (3.7), 46 (2.8) 50 (14.6), 51 (85.7), 52 (5.6), 53 (3.0), 61 (5.6), 62 (17.3), 63 (42.9), 64 (25.4), 65 (11.6), 66 (1.4), 69 (3.6), 74 (9.7), 75 (20.1), 76 (14.0), 77 (24.0), 78 (3.6), 82 (3.1), 86 (2.2), 87 (7.7), 88 (12.1), 89 (100), 90 (24.8), 91 (2.6), 95 (3.4), 98 (1.1), 99 (2.7), 100 (7.3), 101 (49.0), 102 (15.2), 103 (24.6), 104 (2.9), 114 (6.1), 115 (8.0), 116 (84.8), 117 (14.1), 118

(3.5), 127 (9.1), 128 (57.6), 129 (7.4), 130 (29.9), 131 (7.3), 143 (1.0), 144 (33.2), 145 (6.5), 158 (56.8), 159 (6.6), 160 (2.0), 200 (4.3), 259 (93.1), 260 (12.3).

EXAMPLE 5a

Photochemical isomerization of a main fraction containing trans-4-(2,2,3,3-tetrafluoropropoxy)cinnamonitrile 5 g of a mixture of isomers (82.63% by weight of trans- and 17.37% by weight of cis-4-(2,2,3,3-tetrafluoropropoxy) cinnamonitrile) are dissolved in 50 g of methanol and illuminated with a simple UV radiator.

The Table below shows the course of the photochemical isomerization. A conversion takes place which leads to an equilibrium of about 60% by weight of cis- and about 40% by weight of trans-4-(2,2,3,3-tetrafluoropropoxy) cinnamonitrile.

TABLE

| Irradiation period (hours) | cis isomer[1] in % by weight | trans isomer[2] in % by weight |
| --- | --- | --- |
| 0 | 17.37 | 82.63 |
| 1 | 21.5 | 78.5 |
| 7 | 35.6 | 64.4 |
| 11 | 43.4 | 56.6 |
| 17 | 47.8 | 52.2 |
| 25 | 53.2 | 46.8 |
| 33 | 58.07 | 41.93 |
| 41 | 59.15 | 40.85 |
| 57 | 59.4 | 40.6 |

[1] cis isomer = cis-4-(2,2,3,3-tetrafluoropropoxy)-cinnamonitrile
[2] trans isomer = trans-4-(2,2,3,3-tetrafluoropropoxy)-cinnamonitrile As can be seen from the Table, the equilibrium state is almost achieved after an irradiation period of about 30 hours.

During the reaction, decomposition only takes place to a minor extent. The methanolic solution changes color from light yellow to orange-yellow. Analogous photochemical isomerizations of mixtures of arbitrary cis/trans isomer composition always lead to a product which has the previously mentioned equilibrium state of about 60% by weight of cis and about 40% by weight of trans-4-(2,2,3,3-tetrafluoropropoxy)cinnamonitrile.

EXAMPLE 5b

Thermal isomerization of a main fraction containing cis-4-(2,2,3,3-tetrafluoropropoxy)cinnamonitrile 100 g of a main fraction containing cis-4-(2,2,3,3-tetrafluoropropoxy)cinnamonitrile (81.3% by weight of cis- and 18.7% by weight of trans-4-(2,2,3,3-tetrafluoropropoxy) cinnamonitrile) are admixed with 5 g of pyridine and 5 g of piperidine and heated to reflux.

After 5 hours a mixture is obtained which contains the cis and trans isomers in a ratio of 1.8:1 (equivalent to 64.3% by weight of cis-4-(2,2,3,3-tetrafluoropropoxy)cinnamonitrile and 35.7% by weight of trans-4-(2,2,3,3-tetrafluoropropoxy) cinnamonitrile).

This thermally isomerized mixture may be separated again by means of fractional distillation as described in Example 1 and the main fractions arising from this may be further purified by means of fractional crystallization or melt crystallization.

By multiple repetition of the process according to the invention it is possible to convert all of the cis-4-(2,2,3,3-tetrafluoropropoxy)cinnamonitrile into pure trans-4-(1,2,3,3-tetrafluoropropoxy)cinnamonitrile.

EXAMPLE 6

Preparation of 4-(2,2,3,3-tetrafluoropropoxy) cinnamonitrile with addition of a main fraction containing cis-4-(2,2,3,3-tetrafluoropropoxy)cinnamonitrile and thermal isomerization 735.0 g (3.12 mol) of 4-(2,2,3,3-tetrafluoropropoxy) benzaldehyde, 269 g of cyanoacetic acid, 660 g of cis-4-(2,2,3,3-tetrafluoropropoxy)cinnamonitrile (main fractions containing 80 to 85% by weight of cis isomer) are admixed with 750 g of xylene, 750 ml of pyridine and 750 ml of piperidine and heated to 110° C. with stirring. The mixture is allowed to react for 2 hours, and 53.8 g of cyanoacetic acid are added again and the mixture is allowed to react for a further 30 minutes. After cooling, the reaction mixture is distilled under reduced pressure and 1173 g of 4-(2,2,3,3-tetrafluoropropoxy)cinnamic acid (yield: 87% purity>95% by weight) are obtained in the form of a mixture of isomers which contains cis-4-(2,2,3,3-tetrafluoropropoxy) cinnamonitrile and trans-4-(2,2,3,3-tetrafluoropropoxy) cinnamonitrile in a molar ratio of about 1.8:1 and , in addition, about 3% by weight of piperidine and up to 2% by weight of unidentifiable impurities.

As a comparison with the results of the photochemical and thermal isomerizations (Examples 5a and 5b) shows, the reaction mixture obtained almost corresponds to the cis/trans isomer ratio typical of an isomerization. The reaction mixture has a cis/trans isomer ratio of 64.3% by weight: 35.7% by weight, and the product isomerized in accordance with Examples 5a and 5b has an isomer ratio of about 60% by weight of cis isomer to about 40% by weight of trans isomer.

The above described reaction mixture is distilled in a similar manner to Example 1 and 489 g are obtained of a main fraction which contains 82% by weight of trans-4-(2,2,3,3-tetrafluoropropoxy)cinnamonitrile and 18% by weight of cis-4-(2,2,3,3-tetrafluoropropoxy) cinnamonitrile.

The entire first runnings fractions and the bottom product (about 650 to 675 g) are subjected to an isomerization and reused in the fractional distillation. It is also possible to use these products in the actual synthesis and to isomerize them in the course of the synthesis.

EXAMPLE 7

Melt crystallization of the trans-4-(2,2,3,3-tetrafluoropropoxy)cinnamonitrile main fraction obtained from Example 6

The 489 g of main fraction obtained in Example 6 (82% by weight of trans-4-(2,2,3,3-tetrafluoropropoxy) cinnamonitrile: 18% by weight of cis-4-(2,2,3,3-tetrafluoropropoxy)cinnamonitrile) are charged as described in Example 4a into a vertically upright, thermostatable column without internals. After crystallization at 5° C., the temperature is gradually increased and the following fractions are taken off:

up to 45° C. 72 g (38% by weight of trans isomer)
45° to 47° C. 33 g (54% by weight of trans isomer)
47° to 48° C. 22 g (72% by weight of trans isomer)
48° to 49° C. 15 g (81% by weight of trans isomer)
49° to 50° C. 12 g (89% by weight of trans isomer)
>50° C. 335 g (>95% by weight of trans isomer)

We claim:

1. A compound selected from the group consisting of cis-4-(2,2,3,3-tetrafluoropropoxy)cinnamonitrile which has a purity of at least 95% and trans-4-(2,2,3,3-tetrafluoropropoxy)cinnamonitrile which has a purity of at least 95%.

2. The compound as claimed in claim 1, wherein the compound is cis-4-(2,2,3,3-Tetrafluoropropoxy) cinnamonitrile

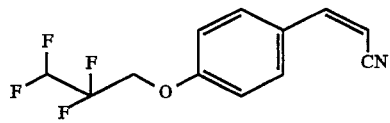

3. The compound as claimed in claim 1, wherein the compound is trans-4-(2,2,3,3-Tetrafluoropropoxy) cinnamonitrile.

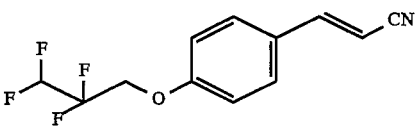

4. The compound as claimed in claim 1, wherein said compound is cis-4-(2,2,3,3-tetrafluoropropoxy)-cinnamonitrile which has a purity of at least 97.5%.

5. The compound as claimed in claim 1, wherein said compound is trans-4-(2,2,3,3-tetrafluoropropoxy) cinnamonitrile which has a purity of at least 97.5%.

* * * * *